United States Patent [19]

Heilman

[11] 4,284,356

[45] Aug. 18, 1981

[54] METHOD OF AND APPARATUS FOR COMPARING SURFACE REFLECTIVITY

[75] Inventor: Richard A. Heilman, Allison Park, Pa.

[73] Assignee: PPG Industries, Inc., Pittsburgh, Pa.

[21] Appl. No.: 78,875

[22] Filed: Sep. 26, 1979

[51] Int. Cl.³ .............................................. G01N 21/86
[52] U.S. Cl. .................................. 356/429; 250/559; 356/430; 356/445
[58] Field of Search ............... 356/390, 429, 430, 431, 356/445, 448; 250/559, 571

[56] References Cited

U.S. PATENT DOCUMENTS

| T932,008 | 3/1975 | Davis et al. | 250/559 X |
|---|---|---|---|
| 2,251,613 | 8/1941 | Kott | 356/448 |
| 2,963,938 | 12/1960 | Irland et al. | 356/341 |
| 3,023,900 | 3/1962 | Thier | 356/430 X |
| 3,572,951 | 3/1971 | Rothwarf et al. | 356/448 |
| 3,666,360 | 5/1972 | Mills et al. | 356/72 |
| 3,792,930 | 2/1974 | Obenreder | 356/239 |
| 4,035,085 | 7/1977 | Seiner | 356/243 |
| 4,072,426 | 2/1978 | Horn | 356/448 |

*Primary Examiner*—Vincent P. McGraw
*Attorney, Agent, or Firm*—Donald Carl Lepiane

[57] ABSTRACT

Light beams directed toward each surface of a sheet are reflected therefrom as first reflected light beams and second reflected light beams. The intensity and/or density of the reflected light beams are acted on to compare the reflectivity of the sheet surfaces, e.g. to determine which surface of the sheet has a more reflective surface.

3 Claims, 3 Drawing Figures

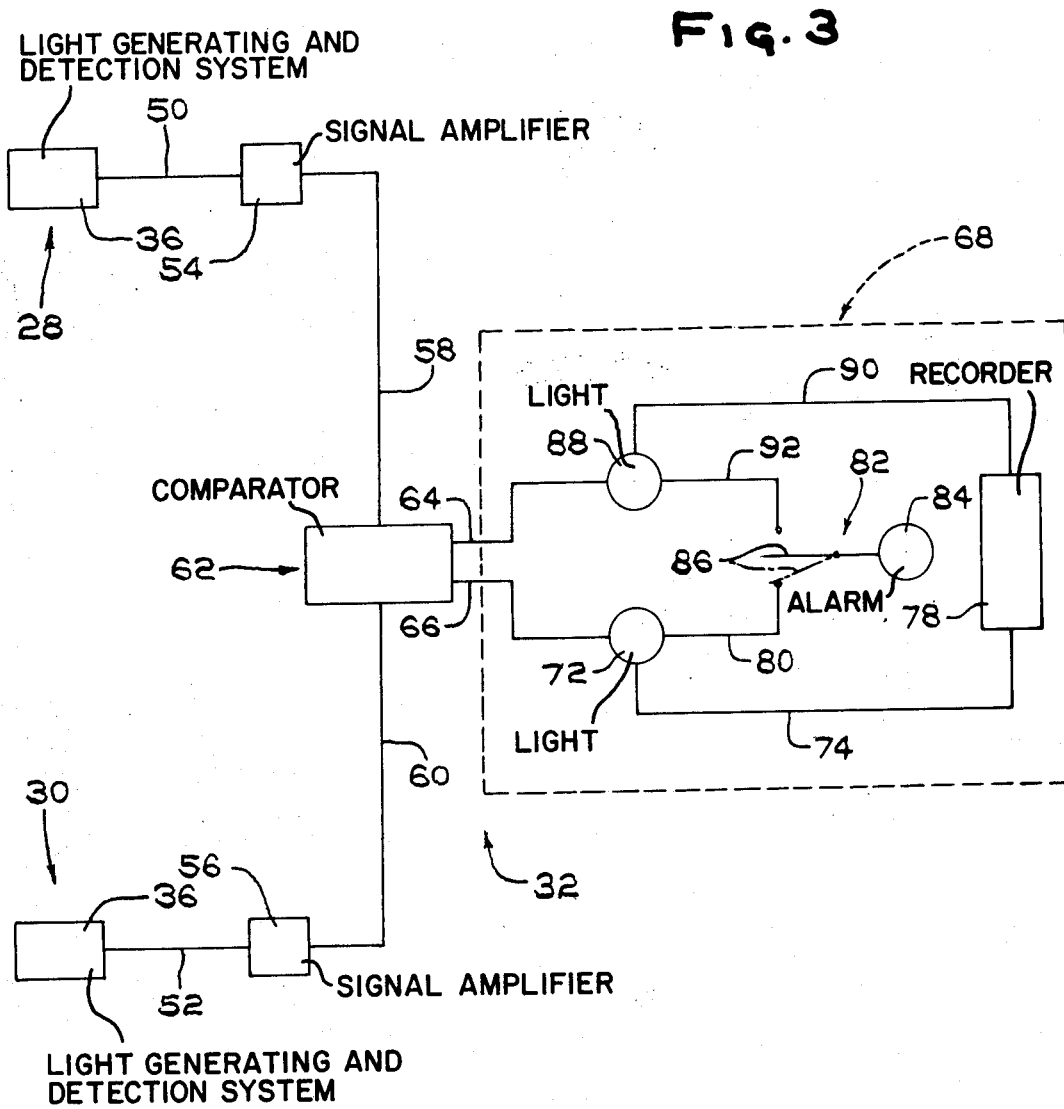

METHOD OF AND APPARATUS FOR COMPARING SURFACE REFLECTIVITY

BACKGROUND OF THE INVENTION

1. Field of the Invention

This invention relates to a method of and apparatus for comparing relative surface reflectivity.

2. Description of the Prior Art and Technical Problems

In the handling of sheets having a coated surface, it is necessary to determine the orientation of the coated sheet surface so that the sheet is properly handled in subsequent operations. There are available in the prior art, e.g., U.S. Pat. Nos. 2,963,938; 3,666,360 and 3,792,930 techniques for inspecting sheets, e.g. glass sheets for internal and external defects. Although the techniques taught in the above-mentioned patents are acceptable for their intended purposes, they are not designed to distinguish between coated and uncoated sheet surfaces. Also in the prior art e.g., U.S. Pat. Nos. 3,572,951; 4,035,085 and 4,072,426 there are taught techniques for inspecting reflective coatings on glass sheet surfaces. Although these systems are acceptable for their intended purposes, there are no teachings therein for adopting these techniques for distinguishing between a coated and an uncoated surface of a glass sheet to determine sheet orientation.

U.S. Pat. No. 2,251,613 teaches a system for determining smoothness of a sheet surface. In general, a light source has its light beams incident on an ink mark on a sheet surface. The light beams of another light source are incident on the opposed surface. The intensity of the reflected beams from each surface are compared to determine the comparative smoothness of the sheet surface. The drawbacks of the system taught in U.S. Pat. No. 2,251,613 are the additional steps required to impose and remove the ink mark and the risk of damaging the surface while the mark is being imposed and/or removed.

From the above it can be appreciated that it would be advantageous to provide a system for comparing and/or distinguishing between reflective surfaces of a sheet.

SUMMARY OF THE INVENTION

This invention relates to a method of comparing reflectivity of opposed surfaces of a substrate, e.g. a glass sheet having a reflective coating on one surface. Energy beams, e.g. light beams of approximately equal intensity are directed toward the opposed sheet surfaces and reflected away from one surface as first reflected light beams and from the opposite surface as second reflected light beams. At least a portion of the first and second reflected light beams are sensed after each have traveled approximately equal distances to compare the reflectivity of opposed surfaces of the glass sheet.

The invention also relates to an apparatus for performing the method and includes facilities for directing light beams toward opposite surfaces of a position in a sheet movement path. Facilities mounted approximately an equal distance from opposed sides of the position sense light beams reflected from one side of the position and beams reflected from the opposite side. Output of the sensing facilities compares reflectivity of opposed surfaces of the glass sheet.

DESCRIPTION OF THE DRAWING

FIG. 3 is a schematic of an electrical system that may be used in the practice of the invention for distinguishing between sheet surfaces.

DESCRIPTION OF THE INVENTION

Figure 1:
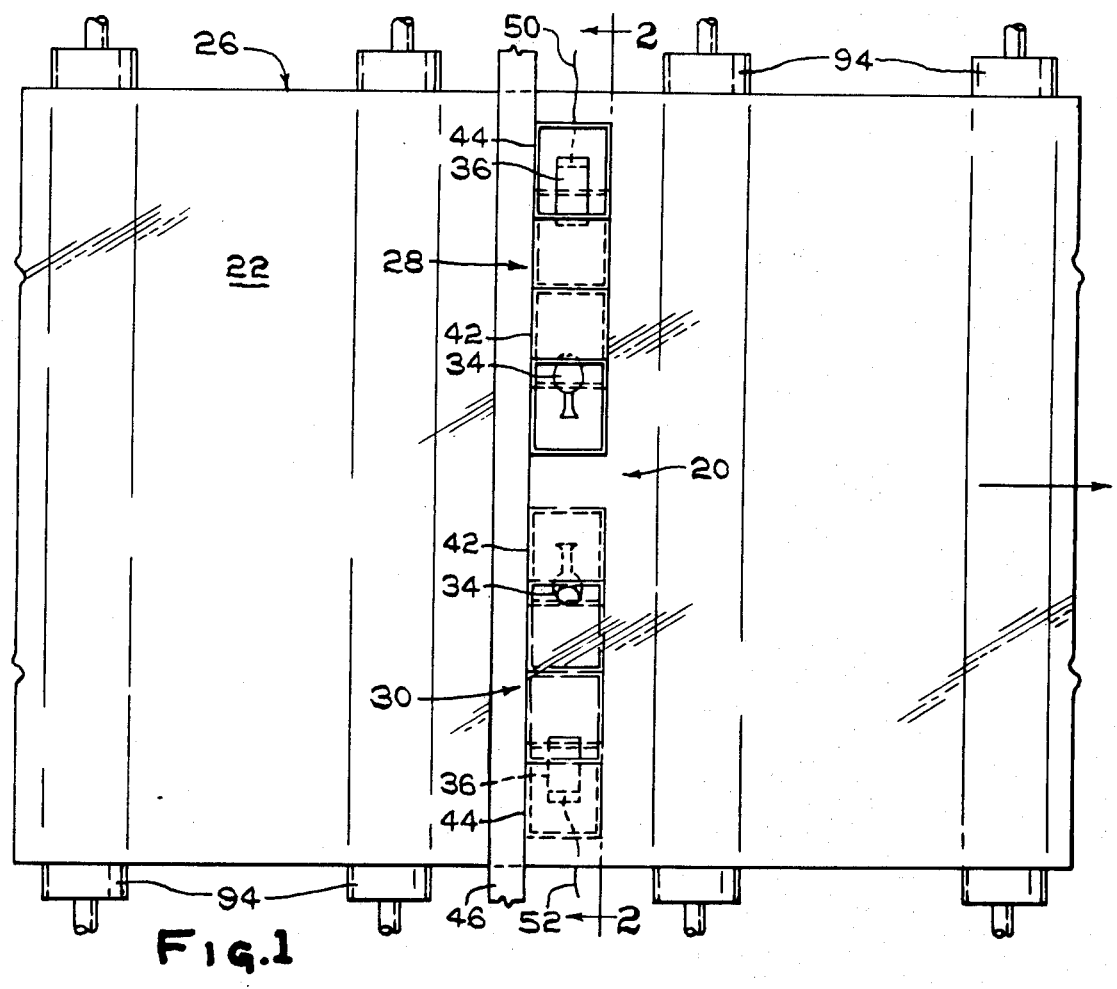
FIG. 1 is a top elevated view of a light generating and detecting system incorporating features of the invention.
Figure 2:
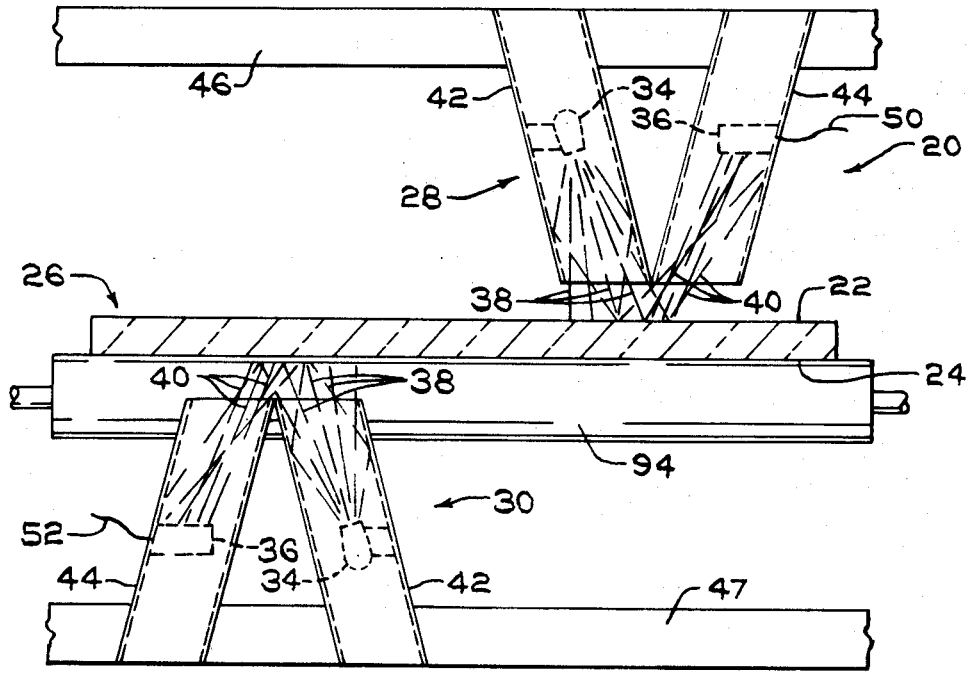
FIG. 2 is a view taken along lines 2—2 of FIG. 1.

Shown in FIGS. 1 and 2 is an apparatus 20 incorporating features of the invention for distinguishing between sheet surfaces, e.g. between top surface 22 and bottom surface 24 of sheet 26. The apparatus 20 as viewed in FIG. 2 has a top and bottom light generating and detecting system 28 and 30, respectively and a signaling system 32 shown in FIG. 3. In the following discussion like numerals refer to like elements. Each of the light generating and detecting systems 28 and 30 include a light source 34 and a light sensitive detector 36. With reference to FIG. 2, light beams 38 from the light source 34 are incident on an adjacent sheet surface 22 or 24 and reflected therefrom as reflected light beams 40 a portion of which are incident on the light sensitive detector 36.

The intensity or density of the reflected light beams 40 can be considered for purposes of this discussion to indicate the reflective condition of the sheet surfaces. For example, if the sheet surface, e.g. top sheet surface 22 reflects more light beams 34 than bottom sheet surface 24 the density or intensity of the reflected light beams 40 from the top surface 22 is greater than the intensity or density of the reflected light beams 40 from the bottom sheet surface 24. The difference in reflectivity between the sheet surfaces can be due to (1) a reflective coating on one sheet surface and not the other sheet surface; (2) depositing a more reflective coating on one sheet surface than on the other sheet surface; (3) polishing only one sheet surface and/or (4) roughening only one sheet surface. If beams reflected from both sheet surfaces have substantially the same density or intensity the reflectivity of the sheet surfaces is substantially the same. The light source 34 is not limiting to the invention and may be a laser, a quartz halogen lamp, a sodium lamp, an Edison bulb and/or a fluorescent bulb. Further, the light beams 38 from the light source 34 may be either columunated light beams or non-columunated, e.g., diffused light beams. The light sensitive detectors 36 are not limiting to the invention and are preferably of the type having an electrical output signal responsive to the intensity or density of light beams incident thereon. Preferably the light source 34 and detector 36 of each system 28 and 30 and adjacent sheet surface 22 and 24 respectively are spaced the same distance. For example, the light source 34 and detector 36 of the system 28 are spaced from one another and adjacent sheet surface 22 the same distance as the light source 34 and detector 36 of the system 30 are spaced from one another and the sheet surface 24. In this manner, the differential effect of travel distance on the light beams 38 and reflected light beams 40 between the systems 28 and 30 is minimized if not eliminated.

The light source 34 and detector 36 are preferably mounted in a tube or housing 42 and 44 respectively to optimize the light generating and detecting systems 28 and 30 by concentrating the light beams and minimize the effect of ambient light. For example, the housing 42 containing the light source 34 has reflective interior walls to increase intensity of light beams 38 incident on adjacent sheet surface. The longitudinal axis of the housing 42 subtends an acute angle with a line normal to the sheet surface 22 or 24 to maximize the intensity and/or density of the light beams 38 and reflected light beams 40. The housing 44 containing the detector 36 also has nonreflective interior walls, e.g. flat back walls to absorb light beams in order that only light beams reflected from the adjacent sheet surface are incident on the detector 36. The angle subtended by the longitudinal axis of the housings 44 and 42 are not limiting to the invention but selected so that the light beams incident on the detector are only those reflected from the adjacent sheet surface. The light source 34 of the system 28 is preferably opposite and adjacent the light source 34 of the system 30 and the systems 28 and 30 are offset from one another as shown in FIGS. 1 and 2 so that stray light from the light source 34 of one system 28 or 30 will not affect the detector 36 of the other system 30 or 28, respectively. The systems 28 and 30 may be mounted in spaced relationship to its respective sheet surface in any convenient manner, e.g. by structural member or bridge 46 and 47 respectively. The bridges 46 and 47 may be mounted for movement relative to the sheet, e.g. as taught in U.S. Pat. No. 3,786,194 which teachings are hereby incorporated by reference, or secured in position in any convenient manner. The sheet 22 may be moved and/or supported between the systems 28 and 30 in any convenient manner.

With reference to FIG. 3 the detectors 36 of the systems 28 and 30 are connected by cable 50 and 52 to signal amplifiers 54 and 56 which are connected by cables 58 and 60, respectively, to a comparator 62. Although not limiting to the invention, the amplifiers 54 and 56 are recommended to increase the normally low output voltage signal from light sensing detectors. The comparator 62 compares the signal received along cables 58 and 60 and forwards a signal along cable 64 and/or cable 66 to indicating system 68 which may include visual indicators, e.g., lamps, audible indicators, such as alarms and/or a recorder. As can be appreciated the invention is not limited to the indicating system 68 which may be any of the types known in the art to indicate that a predetermined event has or has not occured. Further, the comparator 62 may be adjusted to any differential value above which a signal is forwarded to the system 68 to indicate that one surface is more reflective than the other.

As can now be appreciated the invention is not limiting to the sheet material which may be wood, plastic, ceramic, glass-ceramic, glass and/or metal; to the reflective coating on the sheet; the reflective conditioning of the sheet surface and/or manner in which the surfaces are conditioned.

DETAILED DESCRIPTION OF THE INVENTION

The invention is used to indicate proper orientation of a sheet when the coated sheet surface is facing upward as viewed in FIG. 2, i.e. sheet surface 22 has a reflective coating and sheet surface 24 of sheet 26 does not have a reflective coating. With reference to FIGS. 1 and 2 each of the light generating and detecting systems 28 and 30 include a quartz halogen bulb 34, Sylvania Model No. 75Q/CL mounted within a housing 42 and a Selenium Photovotaic Cell 36 of the type sold by Vactec, Inc., Model No. RX80T mounted in a housing 44. The housings 42 and 44 made from about a 2 inch square (5.08 centimeter) aluminum tubing about 6 inches (15.24 centimeters) long are mounted on their respective bridges 46 and 47 with the axial center of the tubing of the housings 42 and 44 of the system 28 and of the system 30 subtending about a 45° angle with one another and about a $22\frac{1}{2}°$ angle with a line normal to the sheet surface 22 or 24. The interior walls of the housings 44 are painted black and the interior walls of the housings 42 are painted white for reasons discussed above. The light source 34 of the system 28 and 30 is spaced about $6\frac{1}{2}$ inches (16.51 centimeters) and the detector 36 of the systems 28 and 30 is spaced about 9 inches (22.86 centimeters) from adjacent sheet surface 22 and 24 respectively. With reference to FIG. 1, the systems 28 and 30 are offset from one another as shown in FIGS. 1 and 2 to prevent the detector 34 of the system 30 or 28 from responding to the light beams 38 of the system 28 or 30, respectively.

With reference to FIG. 3 the detectors 36 of the system 28 and 30 are connected by cables 50 and 52 to an amplifier 54 and 56 respectively. The amplifiers 54 and 56 amplify the input voltage signal by a gain of about 200. The output signal from the amplifiers 54 and 56 is forwarded along cable 58 and 60 respectively to a deviation comparator 62 which compares voltage of the two signals. The comparator 62 compares input signals greater than about 3.6 volts. If the input signal voltage from the cables 58 and 60 are each below 3.6 volts there is no output voltage from the comparator 62. If the signals along cables 58 and/or 60 are/is above 3.6 volts and the input voltage along cable 60 is about 10 percent greater than the input voltage along cable 58, the comparator 62 forwards a signal along cable 66 to energize light 72 of the indicator 68 to indicate that the bottom surface e.g. surface 24 of the sheet 26 as viewed in FIG. 2 has a more reflective coating than the sheet surface 22. Energizing the light 72 forwards a signal along cable 74 to recorder 78 and along cable 80 to switch 82 of alarm 84. The pole 86 of switch 82 is positioned as shown in phantom to electrically connect cable 80 to alarm 84 so that the alarm 84 is energized each time the sheet 26 is misoriented, e.g. the coated sheet surface is facing downward as viewed in FIG. 2. If the signals along cables 58 and/or 60 are/is above 3.6 volts and the input signal along cable 58 to the comparator 62 is at least 10 percent greater than the input signal along cable 60, a signal is forwarded along cable 64 to energize the light 88. Energizing the light 88 forwards a signal along cable 90 to the recorder 78 to provide a cumulative number of properly oriented sheets. In the present arrangement, no voltage signal is forwarded along cable 92 to energize the alarm 84 when the light 88 is energized.

A sheet 26 is moved along a sheet movement path by conveyor rolls 94 between the systems 28 and 30. The light beams 38 from the light source 34 of the systems 28 and 30 are incident on adjacent sheet surface and the reflected light beams 40 are incident on the detector 26 of the systems 28 and 30. The amplified signal of each detectors 36 is received by the comparator 62. If the signals received by the comparator 62 are below 3.6 volts there is no output voltage from the comparator 62 indicating that (1) neither surface of the sheet is coated, (2) the sheet is not positioned between the systems 28 and 30, i.e. there is no sheet in the test position and/or (3) the reflective coating on the sheet surface is not acceptable. If one signal of the signals received by the comparator 62 is greater than 3.6 volts but the difference between the signals is less than 10 percent there is no output signal from the comparator 62 indicating that there is insufficient difference between the sheet surfaces. If in the preceding there is a 10 percent difference in the signals received by the comparator 62 a signal is forwarded along cable 64 or 66 as previously discussed.

As can now be appreciated the above examples are presented for illustration purposes only and are not limiting to the invention.

What is claimed is:

1. A method determining if selected major surface of a glass sheet is properly oriented in a sheet movement path, wherein the glass sheet has a pair of opposed major surfaces having different reflectivity coefficients due to coating on at least one of the sheet surfaces, comprising the steps of:

advancing the sheet along the movement path with a major surface designated as a first sheet surface facing one side of the path and the other major surface designated as a second sheet surface facing the other side of the path;

impinging the first sheet surface and the second sheet surface with diffuse light beams of approximately equal intensity to reflect light beams designated as first reflected light beams from the first sheet surface and light beams designated as second reflected light beams from the second sheet surface;

impinging a portion of the first reflected light beams and of the second reflected light beams onto intensity sensing means after the portion of the first and second reflected light beams have traveled approximately equal distances;

comparing the intensity of the portion of the first reflected light beams to the portion of the second reflected light beams to determine the position in the path of the more reflective sheet surface; and comparing the position in the path of the more reflective sheet surface to a desired position in the path for the more reflective sheet surface to determine if the sheet is properly oriented in the sheet movement path.

2. The method as set forth in claim 1, wherein said comparing the intensity step includes the steps of:

generating a first signal when the reflectivity of the first sheet surface is greater than the reflectivity of the second sheet surface; and generating a second signal when the reflectivity of the second sheet surface is greater than the reflectivity of the first sheet surface.

3. The method as set forth in claim 2, wherein said comparing the position step includes comparing the first signal to the second signal to determine proper orientation of the sheet.

* * * * *